US009107580B2

(12) United States Patent
Goguin et al.

(10) Patent No.: US 9,107,580 B2
(45) Date of Patent: Aug. 18, 2015

(54) DEVICE FOR MEASURING THE ACTIVITY OF THE SPINAL CORD OF A VERTEBRA

(75) Inventors: Alexandre Goguin, Paris (FR); Frederic Lesage, Outremont (CA); Serge Rossignol, Montreal (CA); Habib Benali, Sainte-Genevieve des Bois (FR)

(73) Assignees: UNIVERSITE PIERRE ET MARIE CURIE (PARIS 6), Paris (FR); Polyvalor, Limited Partnership, Montreal (CA); VALORISATION-RECHERCHE, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 13/509,113

(22) PCT Filed: Nov. 10, 2010

(86) PCT No.: PCT/EP2010/006832
§ 371 (c)(1),
(2), (4) Date: Jul. 17, 2012

(87) PCT Pub. No.: WO2011/057765
PCT Pub. Date: May 19, 2011

(65) Prior Publication Data
US 2012/0283572 A1 Nov. 8, 2012

(30) Foreign Application Priority Data
Nov. 13, 2009 (FR) ...................................... 09 05481

(51) Int. Cl.
*A61B 5/00* (2006.01)
*A61B 5/1455* (2006.01)
(Continued)

(52) U.S. Cl.
CPC ............. *A61B 5/0031* (2013.01); *A61B 5/1459* (2013.01); *A61B 5/14551* (2013.01);
(Continued)

(58) Field of Classification Search
CPC .. A61B 5/0031; A61B 5/076; A61B 5/14551; A61B 5/1459; A61B 5/4504; A61B 5/4561; A61B 5/6846; A61B 8/0875; A61B 8/12
See application file for complete search history.

(56) References Cited

U.S. PATENT DOCUMENTS 5,662,122 A * 9/1997 Evans ........................... 600/594
6,122,536 A * 9/2000 Sun et al. ...................... 600/341
(Continued)

FOREIGN PATENT DOCUMENTS

WO 2007/098385 A2 8/2007

OTHER PUBLICATIONS

Andrew J. MacNab, et al., "Near Infrared Spectroscopy for Intraoperative Monitoring of the Spinal Cord", Spine, Lippincott Williams & Wilkins, Inc., Jan. 1, 2002, pp. 17-20, vol. 27, No. 1.
(Continued)

*Primary Examiner* — Ruth S Smith
(74) *Attorney, Agent, or Firm* — Sughrue Mion, PLLC

(57) ABSTRACT

A measurement device for measuring activity of the spinal cord of a vertebrate. The device includes at least one main probe (1) shaped to be fastened to a spinous process (2) of a vertebra (3) and to hold in position on opposite sides of the vertebra at least one emitter (6) for emitting a wave capable of interacting with the spinal cord (7) and at least one associated receiver (8) for receiving the wave that has interacted with the spinal cord and for generating a signal representative of the activity of the spinal cord.

16 Claims, 2 Drawing Sheets

(51) Int. Cl.
A61B 5/1459 (2006.01)
A61B 5/07 (2006.01)
A61B 8/08 (2006.01)
A61B 8/12 (2006.01)

(52) U.S. Cl.
CPC ............ A61B5/4504 (2013.01); A61B 5/4561 (2013.01); A61B 5/6846 (2013.01); A61B 5/076 (2013.01); A61B 8/0875 (2013.01); A61B 8/12 (2013.01)

(56) References Cited

U.S. PATENT DOCUMENTS

| | | | | |
|---|---|---|---|---|
| 6,226,548 | B1 * | 5/2001 | Foley et al. | 600/426 |
| 7,014,633 | B2 * | 3/2006 | Cragg | 604/500 |
| 2006/0036324 | A1 | 2/2006 | Sachs et al. | |
| 2006/0224088 | A1 | 10/2006 | Roche | |
| 2006/0247773 | A1 | 11/2006 | Stamp | |
| 2007/0233065 | A1 * | 10/2007 | Donofrio et al. | 606/61 |
| 2008/0061153 | A1 * | 3/2008 | Hickle et al. | 235/492 |

OTHER PUBLICATIONS

Maryana Simonovich MSC, et al., "Real-Time Monitoring of Mitochondrial NADH and Microcirculatory Blood Flow in the Spinal Cord", Spine, Lippincott Williams & Wilkins, Inc., Jan. 1, 2008, pp. 2495-2502, vol. 23, No. 1.

* cited by examiner

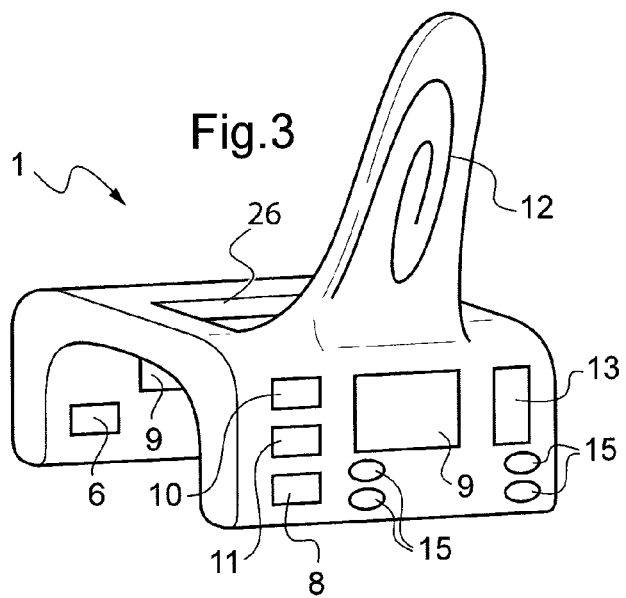
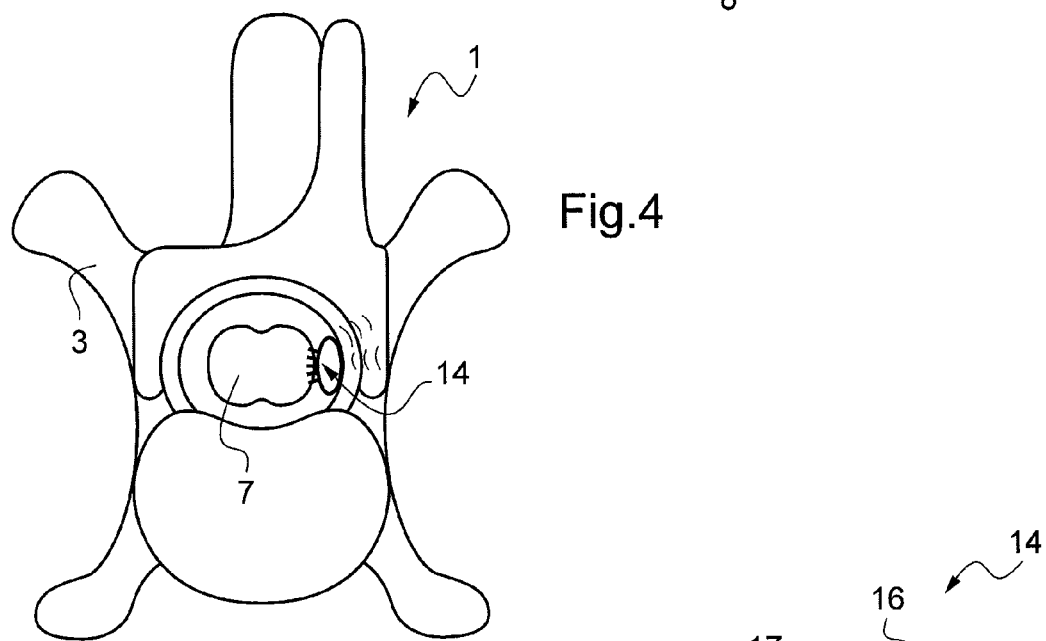
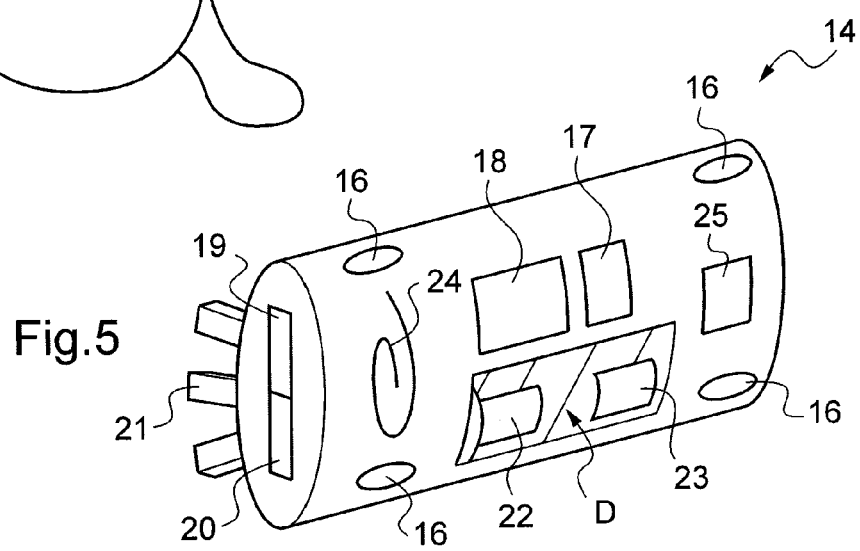

DEVICE FOR MEASURING THE ACTIVITY OF THE SPINAL CORD OF A VERTEBRA

CROSS REFERENCE TO RELATED APPLICATIONS

This application is a National Stage of International Application No. PCT/EP2010/006832 filed Nov. 10, 2010, claiming priority based on French Patent Application No. 09 05481, filed Nov. 13, 2009, the contents of all of which are incorporated herein by reference in their entirety.

The invention relates to a device for measuring activity of the spinal cord of a vertebrate.

The term "activity" is used herein to mean any variation in an optical, chemical, or physical property of the spinal cord that may characterize in particular a neural reaction to a motor or cognitive action.

BACKGROUND OF THE INVENTION

A motor action results from a set of energetic processes leading a nerve signal via the spinal cord to effector organs. A partial or total lesion of the spinal cord leads to a degeneration of the nerve pathways that can no longer transmit signals to the spinal neurons beyond the lesion, which can lead to paralysis and also to an interruption of the upward pathways towards the brain, thereby leading to an abolition of sensation.

Understanding the mechanisms for conveying nerve signals along the spinal column is necessary in order to develop the most effective possible therapeutic treatments.

It is known that variability in the distribution of oxygenated hemoglobin (HbO) and deoxygenated hemoglobin (Hb) can be observed from the blood vessels and capillaries irrigating the neural regions of the cortex and of the spinal column during cognitive or motor activity.

By relying on an optical imaging device that enables these variations in blood volume and oxygenation to be detected, it has been possible to study the neural tissues of the brain. Nevertheless, the technology used is of too great a size to be placed on some other portion of the body or to be implanted continuously in a vertebrate. Whereas trepanation suffices to gain access to brain tissue, gaining access to medullary tissue is more difficult and requires a laminectomy. Finally, the known optical imaging device mainly comprises optical fibers, and such fibers are difficult to use in the spinal cord since their shape makes it difficult for them to be integrated in simple manner in order to measure the hemodynamic response.

At present, the main means for studying the spinal cord as a whole thus remains magnetic resonance imaging (MRI) which enables the cord to be viewed and medullary tissues to be analyzed. Nevertheless, such study remains external, and neural activity perceived in the medullary tissues is scrambled and difficult to interpret from one patient to another.

OBJECT OF THE INVENTION

An object of the invention is to provide an implantable device enabling activity of the spinal cord of a vertebrate to be measured, while overcoming the above-mentioned drawbacks.

BRIEF DESCRIPTION OF THE INVENTION

In order to achieve this object, the invention proposes a measurement device for measuring activity of the spinal cord of a vertebrate, the device comprising at least one main probe shaped to be fastened to a spinous process of a vertebra and to hold in position on opposite sides of the vertebra at least one emitter for emitting a wave capable of interacting with the spinal cord and at least one associated receiver for receiving the wave that has interacted with the spinal cord and for generating a signal representative of the activity of the spinal cord.

The main probe is put into place very simply by making an incision in register with the vertebra concerned and by splaying apart the muscles on either side of the vertebra so that the probe can be placed astride it. All that then needs to be done is to fasten the main probe to the spinous process by means of screws or adhesive. The surgery is thus simple and fast.

BRIEF DESCRIPTION OF THE DRAWINGS

The invention can be better understood in the light of the following description with reference to the figures of the accompanying drawings, in which:

FIG. 3 is a perspective view of the main probe shown in FIG. 1;

FIG. 4 is a cross-section view of a vertebra fitted with a main probe and with an associated auxiliary probe of the invention; and FIG. 5 is a perspective view of the auxiliary probe shown in FIG. 4.

DETAILED DESCRIPTION OF THE INVENTION

The invention is shown in an application to a cat vertebra. This application is naturally not limiting.

Figure 1:
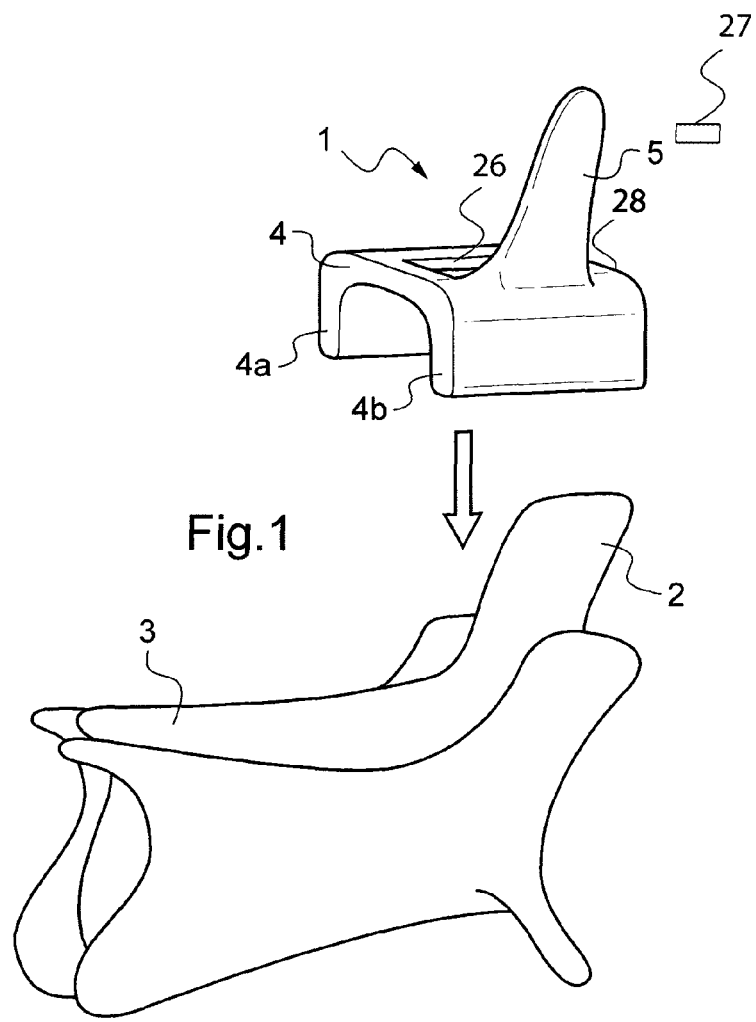
FIG. 1 is a perspective view of a vertebra fitted with a main probe of the invention.
Figure 2:
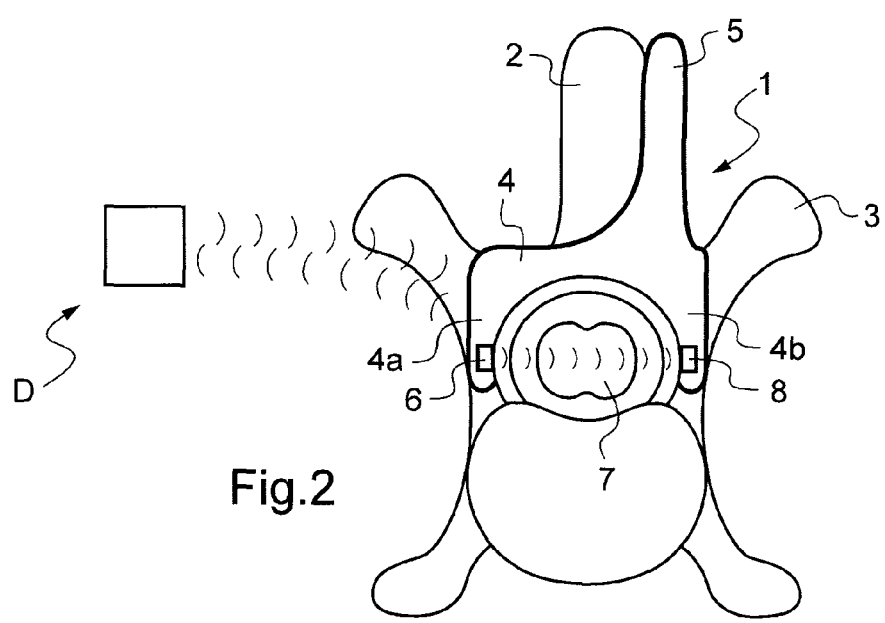
FIG. 2 is a cross-section view of the vertebra fitted with a main probe as shown in FIG. 1.

With reference to FIGS. 1 to 3, the measurement device of the invention comprises a main probe 1 shaped to be fastened to a process 2 of a vertebra 3. The main probe 1, made of a resin that is transparent to infrared radiation, is in the form of a fork 4 having a base 28, two tines 4a, 4b and a handle 5 that extends projecting from the base of the fork 4. The base 28 further has an opening 26 adjacent to the handle 5, the handle projecting asymmetrically relative to a centerline of the base such that the main probe is asymmetric.

This shape enables surgery to be simplified, the surgeon needing to do no more than splay apart the muscles situated on the sides of the vertebra 3 and place the fork 4 on the process 2 in the direction shown by the arrow in FIG. 1. In this position, the fork 4 is astride the portion of the vertebra that forms the medullary canal and the handle 5 extends facing the process 2. The main probe 1 is then preferably fastened via its handle 5 to the process 2, e.g. with a biocompatible adhesive, or indeed with a titanium screw 27.

The tine 4a carries an infrared emitter 6, and the radiation therefrom passes through the spinal cord 7 of the vertebra and, after interacting with the medullary tissue, it is picked up by an infrared receiver 8 carried by the other tine 4b. The infrared radiation passes through the bony wall and interacts with the hemoglobin of the blood contained in the cord 7, thereby making it possible to track vascular activity of the cord 7 when it is stressed. The receiver 8 transforms the radiation it receives into an electrical signal representative of this vascular activity, itself representative of neural activity.

The main probe 1 includes electronic device 9 for transforming this electrical signal into digital data. In this example, the digital data is stored in a memory and transmitted subsequently. For this purpose, the main probe 1 includes an infrared emitter 10 and an infrared receiver 11 for communicating in binary frames with an infrared transceiver remote from the main probe 1. Alternatively, the digital data is transmitted in real time without being stored.

The digital data as generated in this way is advantageously sent to a remote transceiver D in order to track the vascular activity of the spinal cord in response to a simulation thereof. By way of example, the transceiver may be associated with an external control unit adapted to control actuators acting on the organism of the vertebrate in order to mitigate an insufficiency thereof. For example, the control unit may be used to control a pump or an implant delivering a chemical in response to detecting activity of the cord by means of the main probe.

In this example, the main probe 1 is powered electrically from a circuit external to the main probe 1 that delivers a varying magnetic field, thereby causing a current to appear in an antenna 12 that, in this example, is arranged on the handle 5. The electronic device 9 is adapted to condition the potential induced in the antenna 12 so as to produce a potential that is directly usable by the main probe 1. In this example, in order to enable the probe to operate even while distant from the inductive source, it is preferable to use this potential to charge an on-board battery 13.

With reference to FIGS. 4 and 5, and according to a particular aspect of the invention, the remote transceiver D may be associated with an auxiliary probe 14 implanted inside the vertebra 3, so as to come into direct contact with the spinal cord 7. In a preferred mode of implantation, once the muscles surrounding the vertebra have been splayed apart, the surgeon performs a laminectomy on the vertebra, inserts the auxiliary probe 14 in the medullary canal, and reconstructs the vertebra using a polymer resin. With reference to FIGS. 3, 4, and 5, and in a preferred mode of stabilization, the position of the auxiliary probe 14 is stabilized by a magnetic connection with the main probe 1: each probe has magnets 15, 16 with the magnets in a given probe having the same polarity, opposite to that of the magnets of the other probe. The vertebra 3 is sufficiently thin to enable the magnets 15, 16 to attract mutually through the bony wall, thereby stabilizing the auxiliary probe 14 relative to the main probe 1. This fastening is advantageous compared with fastening using surgical sutures in that it simplifies the surgical operation.

The auxiliary probe 14 may perform several functions:
  measuring neural activity of the spinal cord 7. For this purpose, the auxiliary probe 14 includes a sensor 17 responsive to the presence of certain biological molecules in the cerebrospinal liquid, and producing an electrical signal. The auxiliary probe 14 includes electronic device 18 for transforming this signal into digital data; and
  stimulating neural activity of the spinal cord by chemical and/or electrical means. For this purpose, the auxiliary probe 14 includes a tank 19 having a diaphragm and serving to store chemical compounds; a micromotor 20 co-operates with the diaphragm to move it selectively, thereby causing the chemical compounds to be expelled into the spinal cord 7. In addition, electrodes 21 may impose a local potential on the axons of the spinal cord 7 that are in contact with the electrodes 21.

In this example, the transceiver D of the auxiliary probe 14 comprises an infrared emitter 22 and an infrared receiver 23 that communicates by binary frames with the infrared emitter 10 and the infrared receiver 11 of the main probe 1. Thus, no wired connection is needed between the two probes in order to transmit the data generated by the electronic device 18 or to receive orders from the main probe 1. Similarly, the auxiliary probe 14 is powered wirelessly: in a preferred device, an antenna 24 is in communication by induction with the antenna 12 of the main probe 1. The electronic device 18 are adapted to condition the potential induced in the antenna 24 into a potential that is usable directly by the auxiliary probe 14. In this example it is preferable to use this potential for charging an on-board battery 25.

It should be observed that the auxiliary probe needs to be miniaturized because it is implanted very close to the spinal cord, which is an organ that is extremely sensitive. As a result of its size, the length of time the auxiliary probe can run is limited and it needs to be connected to a probe of greater size, here the main probe, in order to be powered regularly.

The invention is not limited to the above description and covers any variant coming within the ambit defined by the claims.

In particular, although it is stated that communication between the auxiliary probe 14 and the main probe 1, and also between the main probe 1 and a transceiver remote from the main probe 1 takes place by infrared radiation, it is possible to use any other mode of communication such as radiofrequency identification (RFID) communication, or indeed for the communication between the main probe 1 and the remote transceiver to be communication by means of wires. Furthermore, although it is stated that the main probe 1 uses a common communications system for communicating with the auxiliary probe 14 and with the transceiver remote from the main probe, it is naturally possible to provide a probe that possesses two distinct communications systems.

Although the main probe 1 is described as having a system for measuring activity of the spinal cord 7 by emitting electromagnetic waves in the infrared, it is possible to use other known techniques, such as emitting ultrasound waves.

Although the auxiliary probe is described as being implanted inside a vertebra 3 in order to be in direct contact with the spinal cord 7, more generally it is possible to implant the auxiliary probe in contact with any functional tissue.

In a variant, it is possible to envisage coupling the auxiliary probe to an osmotic pump of the Alzet type.

What is claimed is:
1. A measurement device for measuring activity of the spinal cord of a vertebrate, wherein the device includes at least one main probe that comprises:
  an emitter that is arranged to emit a wave, and
  a receiver that is associated to said emitter, the receiver being arranged to receive the wave emitted by the emitter,
  wherein the main probe is shaped to be fastened to a spinous process of a vertebra and to hold in position on opposite sides of the vertebra said emitter for emitting a wave capable of interacting with the spinal cord and said associated receiver for receiving the wave, emitted by said emitter, that has interacted with the spinal cord, the receiver being arranged for generating a signal representative of the activity of the spinal cord in view of the wave,
  wherein the main probe is shaped as a fork having:
    two tines, one tine carrying the emitter and the other tine carrying the receiver,
    one base that links the two tines, the base comprising an opening,
    one handle that extends from one side of the opening of the base so that the main probe is asymmetric,
  such that, when the main probe is in position on the vertebra, the fork is astride the portion of the vertebra that forms the medullary canal, the opening extends around the spinous process, and the handle faces the spinous process.

2. The measurement device according to claim 1, wherein the base of the fork extends in a plane that is transverse to a longitudinal direction of the handle and wherein the handle is located to one side of the opening.

3. The measurement device according to claim 1, wherein the wave emitted by the emitter of the main probe and received by the associated receiver is infrared radiation.

4. The measurement device according to claim 1 that comprises a remote transceiver, wherein the main probe includes communications means for communicating remotely with said remote transceiver, the communications means including an infrared emitter emitting signals to the remote transceiver and an infrared receiver receiving signals from the remote transceiver.

5. The measurement device according to claim 4, wherein the remote transceiver is associated with an auxiliary probe adapted for placement in direct contact with a functional tissue, said auxiliary probe including means for stimulating the functional tissue or means for measuring activity of the functional tissue.

6. The measurement device according to claim 5, wherein the auxiliary probe is designed to be placed in contact with the spinal cord, the auxiliary probe and the main probe each comprises at least one magnet, the magnet in the main probe having a polarity opposite to that of the magnet of the auxiliary probe such that the magnets attract mutually, thereby stabilizing the position of the auxiliary probe in the vertebra.

7. The measurement device according to claim 5, further comprising a means for stimulating the spinal cord comprising electrodes for imparting a local potential to axons in contact with the electrodes.

8. The measurement device according to claim 5, further comprising a means for stimulating the spinal cord comprising:
a tank storing molecules, and
means for progressively releasing said molecules stored in said tank into the spinal cord.

9. The measurement device according to claim 5, wherein the auxiliary probe includes inductive means for remotely receiving electrical energy, the inductive means including at least one antenna.

10. The measurement device according to claim 4, wherein the remote transceiver is associated with an auxiliary probe, which is adapted for placement in direct contact with a functional tissue, said auxiliary probe including means for stimulating the functional tissue and means for measuring activity of the functional tissue.

11. The measurement device according to claim 10, wherein the auxiliary probe is designed to be placed in contact with the spinal cord, the auxiliary probe and the main probe each comprises at least one magnet, the magnet in the main probe having the same polarity opposite to that of the magnet of the auxiliary probe such that the magnets attract mutually thereby stabilizing the position of the auxiliary probe in the vertebra.

12. The measurement device according to claim 10, further comprising a means for stimulating the spinal cord comprising electrodes for imparting a local potential to axons in contact with the electrodes.

13. The measurement device according to claim 10, further comprising a means for stimulating the spinal cord comprising:
a tank storing molecules, and
means for progressively releasing said molecules stored in said tank into the spinal cord.

14. The measurement device according to claim 10, wherein the auxiliary probe includes inductive means for remotely receiving electrical energy, the inductive means including at least one antenna.

15. The measurement device according to claim 1, wherein the main probe includes inductive means for remotely receiving electrical energy, the inductive means including at least one antenna.

16. The measurement device according to claim 1, wherein the main probe is configured to be fastened via its handle to said spinous process with biocompatible adhesive or screws.

* * * * *